(12) United States Patent
Monson et al.

(10) Patent No.: US 12,283,823 B2
(45) Date of Patent: Apr. 22, 2025

(54) THERMAL TRANSFER SYSTEM AND METHOD

(71) Applicant: Medtronic, Inc., Minneapolis, MN (US)

(72) Inventors: Robert J. Monson, Minneapolis, MN (US); Andrew T. Fried, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 925 days.

(21) Appl. No.: 17/393,885

(22) Filed: Aug. 4, 2021

(65) Prior Publication Data

US 2023/0040626 A1 Feb. 9, 2023

(51) Int. Cl.
*H02J 50/00* (2016.01)
*A61N 1/375* (2006.01)
*H05K 7/20* (2006.01)

(52) U.S. Cl.
CPC ........ *H02J 50/005* (2020.01); *H02J 50/00* (2016.02); *H05K 7/20336* (2013.01); *A61N 1/375* (2013.01)

(58) Field of Classification Search
None
See application file for complete search history.

(56) References Cited

U.S. PATENT DOCUMENTS

| | | | |
|---|---|---|---|
| 4,071,032 A | 1/1978 | Schulman | |
| 5,991,665 A | 11/1999 | Wang et al. | |
| 6,588,497 B1 | 7/2003 | Glezer et al. | |
| 6,737,618 B2 | 5/2004 | Feucht | |
| 6,894,456 B2 | 5/2005 | Tsukamoto et al. | |
| 7,009,362 B2 | 3/2006 | Tsukamoto et al. | |
| 7,486,048 B2 | 2/2009 | Tsukamoto et al. | |
| 7,891,410 B1 | 2/2011 | Monson et al. | |
| 8,430,644 B2 | 4/2013 | Mahalingam et al. | |
| 9,030,159 B2 | 5/2015 | Chen et al. | |
| 9,227,079 B2 | 1/2016 | Sunagawa et al. | |
| 9,537,344 B2 | 1/2017 | Thompson et al. | |
| 9,592,397 B2 | 3/2017 | Hansen et al. | |
| 9,629,233 B2 | 4/2017 | Saeidi et al. | |
| 9,636,508 B2 | 5/2017 | Chen et al. | |
| 9,717,922 B2 | 8/2017 | Amir et al. | |
| 9,872,997 B2 | 1/2018 | Angara et al. | |
| 9,878,170 B2 | 1/2018 | Angara et al. | |
| 9,905,359 B2 * | 2/2018 | Sultenfuss | H02J 50/12 |

(Continued)

FOREIGN PATENT DOCUMENTS

WO 2022070156 A1 4/2022

OTHER PUBLICATIONS

U.S. Appl. No. 17/393,860, filed Aug. 4, 2021, Monson, et al.

(Continued)

*Primary Examiner* — Leigh M Garbowski
(74) *Attorney, Agent, or Firm* — Harness, Dickey & Pierce, P.L.C.

(57) ABSTRACT

Disclosed is a system for recharging a selected power source wirelessly, such as through a power transmission. The power source may be positioned within a subject and be charged wirelessly through the subject, such as tissue of the subject. A thermal transfer system is provided to transfer or transport thermal energy from a first position to a second position, such as away from the subject.

20 Claims, 4 Drawing Sheets

(56) References Cited

U.S. PATENT DOCUMENTS

| | | |
|---|---|---|
| 10,293,174 B2 | 5/2019 | Amir et al. |
| 10,434,235 B2 | 10/2019 | Hansen et al. |
| 10,810,614 B2 | 10/2020 | Angara et al. |
| 2013/0096646 A1 | 4/2013 | Yildirim et al. |
| 2013/0323099 A1 | 12/2013 | Li et al. |
| 2014/0002990 A1 | 1/2014 | Sharma et al. |
| 2016/0360606 A1 | 12/2016 | Saeidi et al. |
| 2017/0063101 A1 | 3/2017 | Sultenfuss et al. |
| 2017/0274778 A1 | 9/2017 | van Boheemen et al. |
| 2019/0022394 A1 | 1/2019 | Fayram et al. |
| 2021/0176894 A1 | 6/2021 | Yalamarthy et al. |
| 2023/0040626 A1 | 2/2023 | Monson et al. |
| 2023/0045399 A1 | 2/2023 | Monson et al. |
| 2024/0024156 A1* | 1/2024 | Vavelin ................. H02J 50/005 |

OTHER PUBLICATIONS

U.S. Appl. No. 17/393,965, filed Aug. 4, 2021, Monson, et al.
International Search Report and Written Opinion regarding International Patent Application No. PCT/US2022/037039, dated Oct. 18, 2022.

* cited by examiner

THERMAL TRANSFER SYSTEM AND METHOD

CROSS-REFERENCE TO RELATED APPLICATIONS

This application includes subject matter related to concurrently filed U.S. patent application Ser. No. 17/393,860 filed Aug. 4, 2021 and U.S. patent application Ser. No. 17/393,965 filed Aug. 4, 2021. The entire disclosures of each of the above applications are incorporated herein by reference.

FIELD

The subject disclosure relates to a cooling and/or heat dissipation system, and particularly to a thermal energy transfer and a charging system.

BACKGROUND

This section provides background information related to the present disclosure which is not necessarily prior art.

A device may be positioned in a subject, such as a human subject, for providing therapy to the subject. Therapy may include substance delivery from a reservoir, stimulation from a power source, or other appropriate therapies. In various instances, the implanted device may include a battery that may be recharged from an external charger.

The external recharger may include the Activa® RC Recharger Model WR9200 sold by Medtronic, Inc. having a place of business in Minnesota. The recharger may include an antenna that transmits a signal, also referred to as a power transfer signal, to inductively charge the battery in the implanted device. The recharger may be positioned relative to the implanted device to transmit the signal in an appropriate manner, such as placing it over the device a selected distance from the implanted device.

SUMMARY

This section provides a general summary of the disclosure, and is not a comprehensive disclosure of its full scope or all of its features.

An implantable device, also referred to as an implantable medical device (IMD) which may include an implantable neurostimulator (INS) for a deep brain stimulation (DBS) system may be provided. The IMD may be positioned within a subject, such as a human patient or other living patient, at a selected time. The IMD may include a power source, such as a battery (e.g., chemical cell) for powering various components of the IMD. For example, a controller may control stimulation of a plurality of leads or electrodes by providing a power signal from the power source. It is understood, however, that the disclosed system may be placed in any appropriate system, such as an airframe or robotic system. The system may be placed as a power system that may be recharged at a selected time, as discussed herein.

The power source may be drained over a selected period of time due to providing therapy, such as stimulation, to the subject. The power source may, therefore, be replaced and/or recharged. In various embodiments, the power source may be recharged rather than being replaced.

The power source may be recharged wirelessly through a power transfer signal. The power transfer signal may be any appropriate type of signal such as an inductive transfer of energy to the battery. For example, an inductive charger may be positioned relative to the IMD to transmit a signal to generate a current for charging the power source. In charging the power source, a temperature increase may occur due to thermal energy generation due to the generation of the charging signal.

A heat dissipation or thermal dissipation system may be positioned relative to the transmitter at the recharger. The recharger may be movable relative to the subject and external to the subject such that a portion, such as a majority of the outer surface of the recharger, may be open to an environment (e.g., air) or positioned a distance from the subject. The cooling system may be positioned to transfer thermal energy from the antenna of the recharger to an area or volume away from the antenna and, therefore, away from the subject.

The thermal transfer may include a heat sink and heat pipe system. The heat sink may be positioned near to and/or in contact with the antenna. The heat pipes may be positioned near to and/or in contact with the heat sink. The heat sink may transfer (e.g., absorb) thermal energy from the antenna. The heat pipes may transfer thermal energy from the heat sink to a space away from the antenna and, therefore, away from the subject. Therefore, thermal energy may be moved aware from adjacent to the subject to maintain a selected temperature at the surface of the subject and/or between the recharging device and the surface of the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
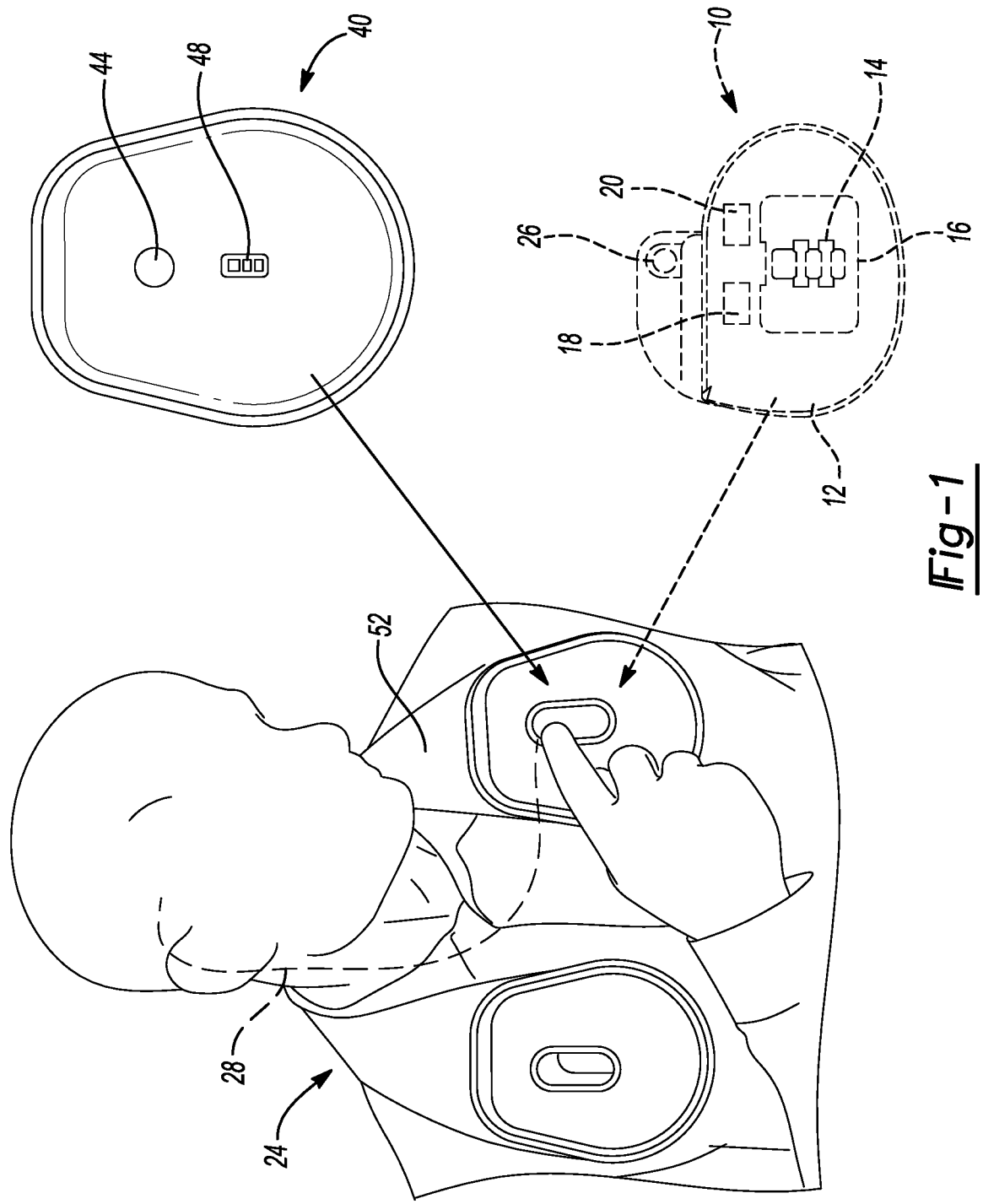
FIG. 1 is an environmental schematic view of a subject with an implantable device and a wireless recharger.
Figure 2:
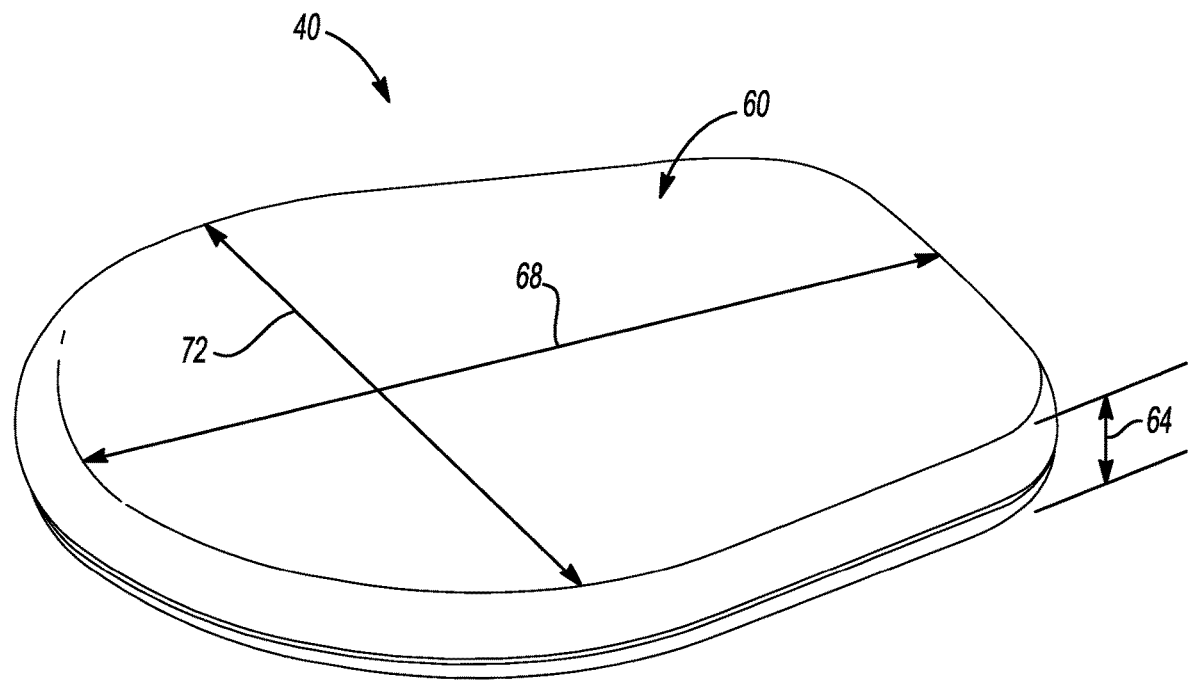
FIG. 2 is a perspective view of a wireless charger, according to various embodiments.

With initial reference to FIG. 1, an implantable device (IMD) 10 may include a case or shell portion 12 that may incorporate or include a power source 14, such as a capacitor, an energy cell, etc. and an antenna 16, a processor assembly 18, and a memory 20. The antenna 16 may be for transmitting a signal, receiving a signal, and/or receiving a power transfer signal for recharging the power source 14. The antenna 16 may have selected dimensions such as a diameter that is about 5 centimeters (cm) to about 12 cm, including about 6 cm to about 8 cm. It is understood that the IMD 10 may include additional components, as is understood by one generally skilled in the art, but may not be relevant for the subject disclosure. The IMD 10 may include the Activa® Implantable Medical Device sold by Medtronic, and having a place of business in Minnesota. The IMD 10 may include the components of the Activa® IMD as is generally understood by one skilled in the art. Accordingly, the IMD 10 may include components relevant for providing therapy to a subject 24.

Further, the IMD 10 may include outputs or connection portions 26 that allow for connection of various implanted devices, such as deep brain stimulation probes 28 that may be positioned in the subject 24 for providing therapy to the subject 24. It is understood, however, in various embodiments that the IMD 10 may provide a substance delivery system including a pump, a reservoir, and various catheters to deliver material to the subject 24 in a selected sequence. Further, the IMD 10 may be cardiac pacing and/or defibrillator. In various embodiments, the processor system 18 may control various components the IMD 10 to provide therapy to the subject 24 and/or for various other purposes such as controlling or assisting in controlling recharging of the battery 14.

The power source 14 may exemplary be a cell and may include a chemical battery, such as a lithium ion battery and may be referred to herein as battery 14. It is understood that other appropriate energy storage devices may also be provided within the IMD 10 to provide energy to the IMD 10 for providing therapy to the subject 24. The battery 14, however, may become discharged over a period of time. Moreover, the battery 14 or any appropriate power source may be positioned within a subject at any appropriate time and may be recharged, as discussed herein, for any appropriate purpose.

A wireless recharger system 40 may be provided to recharge the battery 14 of the IMD 10. The IMD 10 may be positioned within the subject 24 at a selected time and at a later time, such as days, weeks, months, or other appropriate time thereafter the battery 14 of the IMD 10 may be recharged. The recharger system 40 may be positioned relative to the subject 24, as illustrated in FIG. 1 to recharge the battery 14. The recharger system 40 may be positioned relative to a surface, such as on or near a skin surface or clothing surface of the subject 24 to provide the power transfer signal, also referred to as a recharging signal, to the antenna 16 of the IMD 10. The recharging signal may provide a recharging current for recharging the battery 14 at a selected rate. It may be selected to maintain a selected temperature range and/or limit a maximum temperature at the surface of the subject 24. Therefore, recharge times may be limited or cycled. As discussed herein, a heat transfer system may also be provided to move thermal energy to cool the surface of the subject 24 and/or portions of the recharger assembly 40.

The recharger system 40 may include a various control inputs, such as a button 44, or other appropriate inputs and/or outputs such as a display 48 that may display the power left in the recharging battery, or other appropriate systems. The recharger system 40 may further include an antenna for receiving wireless control signals, such as from a portable device (e.g., a tablet, a portable phone, etc.). Further, a wired connection may be made to the recharger system 40 providing inputs and/or controlling the recharger system 40.

The recharger system 40 may be provided within a harness or collar 52 that may position the recharger system 40 relative to the subject 24. In an appropriate location, such as with the harness 52, the recharger system 40 may be positioned to recharge the IMD 10 once positioned within the subject 24. The recharger system 40 may also be free handheld, etc. for recharging.

The recharger system 40 may include a housing 60 that has selected dimensions such as a height or depth dimension 64. The height dimension 64 may be about 0.2 centimeters (cm) to about 8 cm, including about 0.5 cm to about 4 cm, including about 2.5 cm. The housing may further include various dimensions such as a first side length 68 and a second side length 72. The first side length 68 may have selected dimensions such as about may be about 8 cm to about 15 cm, including about 11 cm to about 14 cm, including about 13 cm. In various embodiments, the second side length 72 may have a dimension about 6 cm to about 13 cm, including about 8 cm to about 12 cm, including about 10 cm. It is understood that various manufacturing and/or design considerations may be included or incorporated such that dimensions, as discussed herein, may vary by about 0.01 inches to about 0.5 inches.

The housing 60 may include a top portion 60a and a bottom portion 60b. The two portions may be fixed together, such as with welding, snap fit, adhesives, or the like. Nevertheless, the recharger system 40 may be moved relative to the subject 24 in any appropriate manner. The housing 60 may have various components provided between or within the housing 60. For example, a battery 80 may be provided within a housing 60 to provide energy to energize and power components of the recharger system 40, such as to provide the power transfer signal. A battery recharging assembly or components, such as a contact 84 may be provided in the housing 60 to recharge the battery 80. Recharging the battery 80 may be via a corded recharging system using a cord 88 to provide power to recharge the battery 80.

The recharger system 40 may include a transmitting antenna 92 to transmit the power transfer signal to the antenna 16 of the IMD 10 to recharge the battery 14. The antenna 92 may be a coil that has a diameter of a selected dimension, such as about 8 cm to about 16 cm, including about 10 cm to about 12 cm. A control system 96 may be provided with the recharger system 40 that may include a processing system or assembly 98 and a memory system or component 100. Other appropriate components may also be provided in the control system to allow for controlling the recharging assembly 40 to recharge the battery 80, generating the power transfer signal to recharge the battery 14 of the IMD 10, or other appropriate components understood by one skilled in the art. For example, a driver 104 may be provided to drive a current through the coil 92. The driver 104 may be operated to drive a current from the battery 80 through the coil 92 to generate the power transfer signal.

The control system 96 may be interconnected between the antenna 92, the battery 90, and various other components, such as the input 44. As discussed above, the input 44 may include one or more input portions to control the recharger system 40. The recharger system 40 may include a wireless or wired communication system to receive inputs and transmit data for controlling the recharger system 40, such as a recharging rate, etc. The wireless connection may include the antenna 92 and/or a separate antenna 104 that may include wireless communication or various protocols, as understood by one skilled in the art.

Accordingly the recharger system 40 may include the antenna (also referred to as a charging coil recharge energy transmitter) 92 to provide a power signal for recharging the battery 14 of the IMD 10. A thermal energy or heat transfer assembly 110 may also be provided. The heat transfer assembly may include one or more members, such as a single or monolithic member 114 that may be positioned in contact or substantially adjacent to the antenna 92. The member 114 may also be referred to as a heat sink 114. The heat sink may be formed of a selected material, such as a ferrite material. The heat sink may also be an appropriate heat transfer material including copper, silver, iron, etc., and/or combinations of the above. Generally, the heat sink 114 may have a dimension that is substantially the same as the antenna 92. For example, the heat sink 114 may have an area that is about 80% of the antenna to about 200%, plus or minus about 50%. Generally, the heat sink 114 includes enough mass to absorb heat generated by the source, such as the antenna. Also, the heat sink 114 may include or be formed as a substantially monolithic or single piece member. In various embodiments, however, the heat sink 114 may be formed of a plurality of members that are then fixed together, such as with adhesives, solder, etc.

The heat transfer assembly 110 may further include one or more heat transmitting or thermal transmitting portions 118. As discussed further herein, for example, the heat transmitting portion 118 may include heat pipes also referred to as heat pipe tubes. The heat pipes 118 may include heat pipes such as those formed of copper or copper alloys. Exemplary heat pipes include the heat pipe model ATS-HP-D4L200G30 W-001 sold by Advanced Thermal Solutions, Inc. Heat pipes may be formed of selected materials, such as copper, diamond, and/or gold. In various embodiments, diamond can be deposited on a surface and produce a very effective heat channel.

The heat pipes 118 may include a selected geometry and dimensions, as discussed herein. Generally, the heat pipes 118 may contact and/or connect to the heat sink 114 and extend away therefrom. It is further understood by one skilled in the art that the number of the heat pipes 118 may be selected based on various considerations such as a geometry of the recharger system 40, the housing 60, the antenna 92, heat transfer rate, etc. Therefore, the number of heat pipes 118 discussed herein is merely exemplarily, unless specifically stated otherwise in a particular embodiment.

Figure 3:
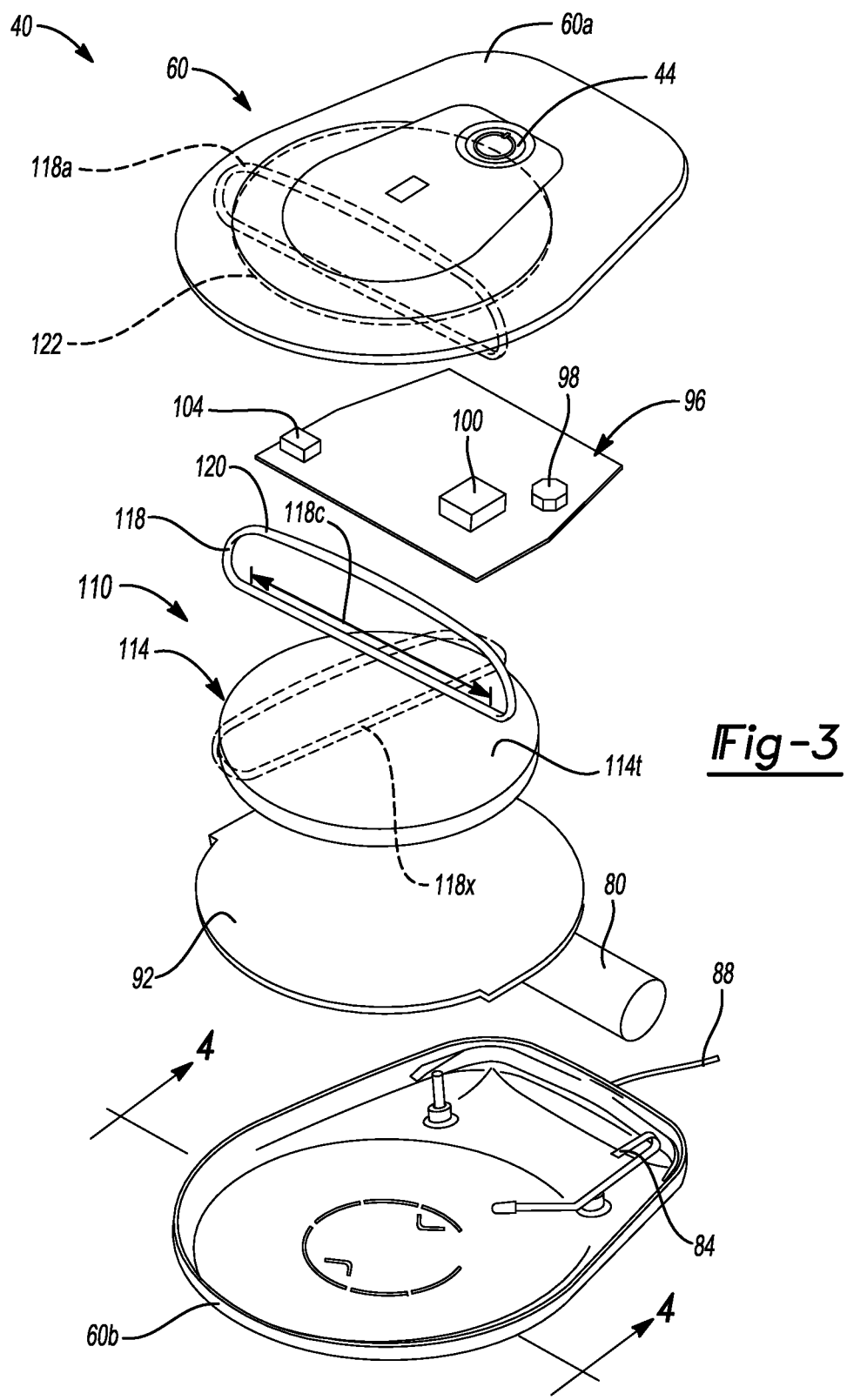
FIG. 3 is an exploded view of the wireless charger of FIG. 2, according to various embodiments.
Figure 4:
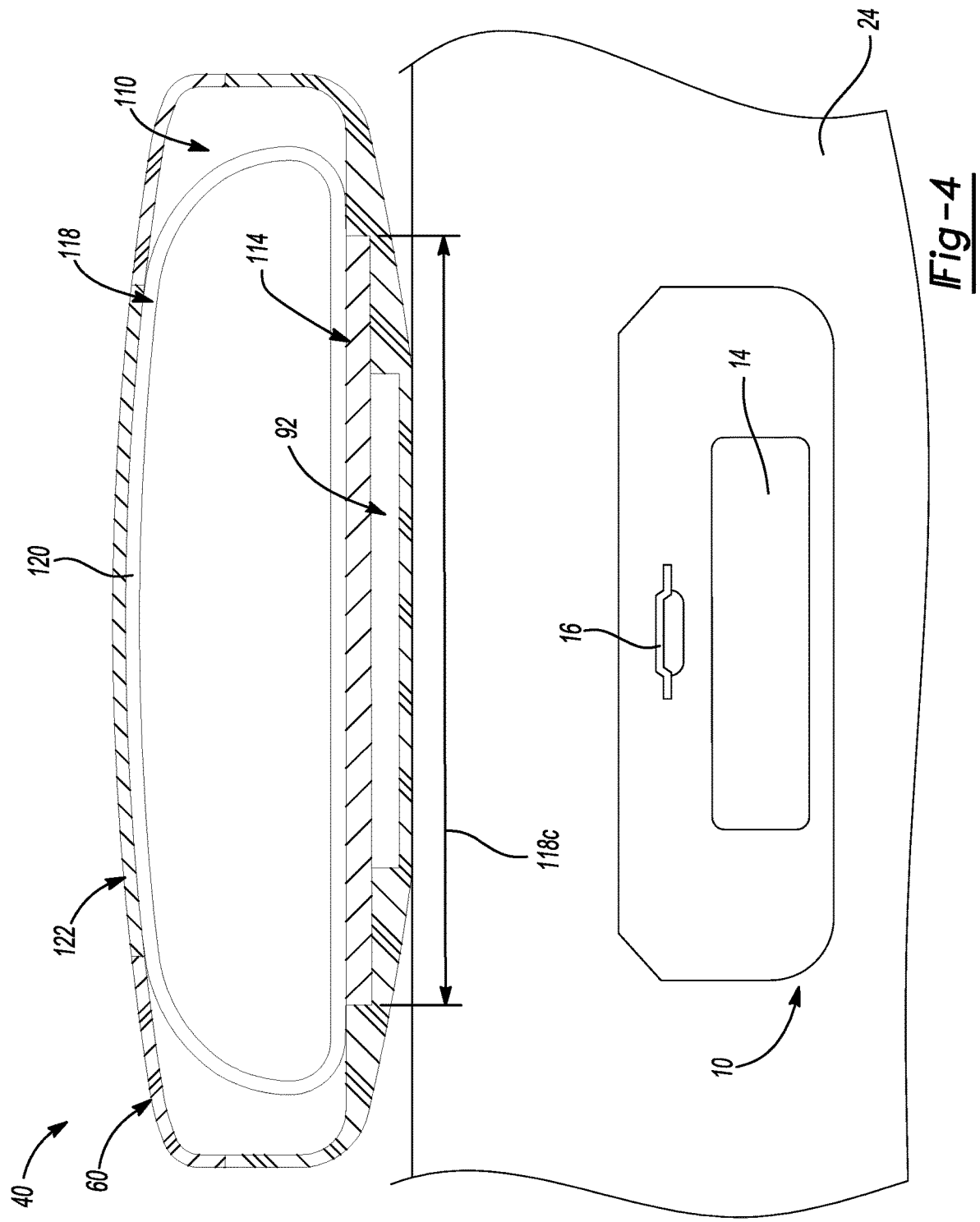
FIG. 4 is a cross-sectional view of the recharger, according to various embodiments.

Further, the heat pipes 118 extend away from the heat sink 114, such as above the PCB 96 and toward the case top 60a. As illustrated in FIG. 3, for example, an exemplary second heat pipe, also referred to as a heat pipe tube, 118a is illustrated to extend near or toward the case top 60a above or away from the PCB 96. When assembled, the heat pipe 118a may extend away from the heat sink 114 at a second position a distance away from the heat pipe 118 and also away from the heat sink 114, as illustrated in FIG. 4.

The heat pipe system may include the heat pipes 118 formed or placed in a first direction. Further, or additional heat pipes 118x may also be provided at angles relative to the other heat pipes, such as orthogonal. Thus, the heat pipe system paths may be formed as a lattice or other appropriate configuration.

As discussed above, the heat pipes 118, 118a, when assembled in the recharger assembly 40 within the housing 60, may be positioned to be near or in contact with a top surface 114t of the heat sink 114. In various embodiments, for example, the heat pipes 118, 118a may include a geometry that allows for a substantial contact surface area between the top surface 114t of the heat sink 114 and the respective heat pipes 118, 118a. Accordingly, the heat pipes 118, 118a may include a portion or a length that is a contact length 118c or section that is in contact with the top surface 114t of the heat sink 114. For example, the contact length 118c may be linear to contact a flat portion of the top surface 114t. Therefore, the amount of contact to allow for thermal energy transfer from the heat sink 114 to the heat pipe 118 may be maximized.

Further, the heat pipes 118, 118a may include a top or spaced apart portion 120 that may be at the top or near the top 60a of the housing 60. Therefore, thermal energy may be transferred away from the heat sink 114 to a position away from the heat sink 114 within the housing 60. An additional member which may be referred to as a heat spreader and/or secondary heat sink 122 may be provided, in various embodiments, at or near the top 60a. The heat pipes 118, 118a may contact or be positioned adjacent to or near the heat spreader 122. The heat spreader 122 may have a thermal conductivity to assist in transferring thermal energy from and away from the heat pipes 118a, 118. Therefore, the differential between the heat sink 114 and the heat pipe tops 120, 120a may be further enhanced or increased. Thus, the transfer of thermal energy from the heat sink 114 to a position away from the heat sink 114 may be increased. The spreader 122 may be formed of a selected material, such as solid or porous copper, copper alloys, or other materials that may be transparent to the power transfer signal and/or other wireless signals relative to the recharger system 40.

The heat pipes 118, 118a may include internal passages that define a volume that allow for holding or positioning a selected volume of a fluid therein. The fluid may be moved within or change states within the heat pipe passage of the heat pipes 118, 118a as is generally understood by one skilled in the art. Therefore, the heat pipes 118, 118a may be used to transfer the thermal energy such as through phase changes of the fluid within the heat pipe at the position from near the heat sink 114 to the position near the top 60a and/or the spreader 122.

The heat pipes 118, 118a may be fixed to the heat sink 114 in any appropriate manner. For example, the heat pipes 118, 118a may be solder, brazed, welded, or otherwise connected to the heat sink 114, such as at the top surface 114t. Appropriate methods that allow for efficient and/or fast heat transfer to the heat pipes 118, 118a may be used.

The heat pipes 118 may also be provided in a selected form and/or configuration. For example, a continuous loop may be formed through each heat pipe 118. The heat pipe 118 may form a single loop. Therefore, the heat pipes 118 may be provided in parallel. In various embodiments, however, the plurality of heat pipes may be provided in series such that the all or a portion of the heat pipes 118 are interconnected. It is further understood that any appropriate number of the heat pipes may be provided, and two is provided merely for the current disclosure. Further, the heat pipes 118 may be formed in selected geometries and/or patterns on the heat sink 114. For example, the heat pipes may be formed in an interconnecting pattern, such as a waffle or grid pattern.

With continuing reference to FIG. 3 and additional reference to FIG. 4, the housing 60 of the wireless recharger 40 may house or encompass the heat transfer assembly 110 including the heat sink 114 and the heat pipes 118. Further, the housing may encompass the recharger coil 92 and the PCB 96 and associated portions. Accordingly, as the recharging coil 92 is positioned in contact with the patient 24, such as at a contact surface 130 of the patient 24, the recharging coil 92 may transmit a the power transfer signal that is received by the antenna 16 within the IMD 10 to recharge the battery 14 within the IMD 10. During the transmission, a thermal energy may be generated at the recharging coil 92. The heat sink 114 in contact or adjacent to the recharging coil 92 may conduct or absorb some of the thermal energy. The heat sink 114, therefore, may therefore increase in temperature.

Nevertheless, the heat pipes 118 of the heat transfer system 110 may be used to transfer thermal energy from the recharging coil 92 such as to or at the top of the case 60a including a top surface or area 134. Therefore, the thermal energy may be radiated into an environment away from the patient 24, such as the contact surface 130. By moving the thermal energy away from the recharging coil 92 the temperature at the contact surface 130 may be reduced or minimized during operation of the transmitting coil 92 to generate the power transfer signal.

As is understood by one skilled in the art, the passage through the heat pipe 118 may include a fluid, such as water. A difference in temperate between two points in the system causes a change in the state and/or pressure of the fluid. It is understood by one skilled in the art, however, that the points may not be static as heat is transferred. The temperature change cases a change in state and pressure of the fluid within the system to transfer the thermal energy. At a certain or selected time, the fluid may evaporate at the first point and condense at the second point. As the passage is continuous in the heat pipe 118 this may occur anywhere within the system of the heat pipe 118.

The transmitter coil 92, therefore, may be operated at extended intervals to provide for charging of the battery 14 of the IMD 10 at a selected speed or reduced time. Further, the power transfer signal may be greater while maintaining a selected temperature at the contact surface 130. As understood by one skilled in the art, the heat transfer system 110 may be provided in the wireless recharging assembly 40 to transport thermal energy from a first position, such as at the transmitter coil 92, to a second position, such as at the surfaced 134 away from the contact surface 130.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system for transferring thermal energy in a wireless recharger for an implantable system, comprising:
   a transmitter coil configured to transmit a power transfer signal;
   a power source to energize the transmitter coil to transmit the power transfer signal;
   a heat sink having a first side adjacent the transmitter coil and a second opposed side and configured to absorb thermal energy from near the transmitter coil; and
   a heat pipe separate from and spaced away from the transmitter coil, the heat pipe defining an internal heat pipe passage;

wherein the heat pipe includes a first portion positioned near the second opposed side to absorb thermal energy from the heat sink and a second portion positioned away from the heat sink, wherein thermal energy is transported from the first portion of the heat pipe to the second portion of the heat pipe.

2. The system of claim 1, further comprising:
a housing that houses all of the transmitter coil, the heat sink, and the heat pipe;
wherein the housing includes a subject side and an environment side;
wherein the transmitter coil is positioned at the subject side and transmits the power transfer signal to a receiving coil within the subject;
wherein the heat pipe extends from the heat sink to the environment side, wherein the environment side is spaced away from the transmitter coil.

3. The system of claim 2, further comprising:
a control system configured to control the energizing of the transmitter coil;
wherein the control system is included within the housing.

4. The system of claim 2, wherein the heat pipe includes a plurality of heat pipes.

5. The system of claim 4, wherein plurality of heat pipes define a plurality of heat pipe paths or a single heat pipe path longer than any one of the heat pipes.

6. The system of claim 4, wherein each heat pipe of the plurality of heat pipes is a separate continuous heat pipe and extends a distance away from the heat sink.

7. A system for transferring thermal energy, comprising:
a transmitter coil configured to transmit a power transfer signal when energized by a power source and positioned near a subject surface;
a heat sink formed of a ferrite and having a first side adjacent the transmitter coil and configured to absorb thermal energy from the transmitter coil and an opposed second side; and
a heat pipe separate from and spaced away from the transmitter coil, the heat pipe defining an internal heat pipe passage;
wherein the heat pipe includes a first portion positioned relative to the second side of the heat sink to absorb thermal energy from the heat sink and a second portion positioned away from the heat sink;
wherein the heat pipe is configured to transport thermal energy away from the heat sink and reduce a temperature at the subject surface.

8. The system of claim 7, wherein the heat pipe includes a plurality of heat pipes.

9. The system of claim 8, wherein the each heat pipe of the plurality of heat pipes is separate and continuous and positioned in parallel with each of the other heat pipes.

10. The system of claim 8, wherein at least two heat pipes of the plurality of heat pipes are connected in series with each other.

11. The system of claim 8, further comprising:
a housing that houses all of the transmitter coil, the heat sink, and the plurality of heat pipes;
wherein the housing includes a subject side and an environment side;
wherein the subject side is configured to be positioned near the subject surface to transmit the power transfer signal into the subject and to a receiving antenna;
wherein the plurality of heat pipes extend to the environment side from away the heat sink.

12. The system of claim 7, further comprising:
a spreader plate positioned near the second portion and configured to absorb thermal energy from the heat pipe;
wherein the spreader plate has a thermal capacity greater than the second portion of the heat pipe.

13. The system of claim 7, further comprising:
a driver configured to drive the power signal through the transmitter coil; and
the power source to energize the transmitter coil to transmit the power transfer signal.

14. A method of transferring thermal energy in a wireless recharger for an implantable system, comprising:
providing a heat sink having a first side near a transmitter coil and a second side, wherein the transmitter coil is configured to transmit a power transfer signal when energized by a power source;
providing the heat sink to absorb thermal energy from the transmitter coil at the first side; and
providing a heat pipe path with a heat pipe separate from and spaced away from the transmitter coil and from the heat sink to a position away from the heat sink.

15. The method of claim 14, further comprising:
contacting the second side of the heat sink with a first portion of the heat pipe;
positioning a second portion of the heat pipe a distance from the heat sink.

16. The method of claim 14, further comprising:
providing the heat sink formed of a ferrite.

17. The method of claim 14, wherein providing the heat pipe path with the heat pipe includes providing a plurality of separate heat pipe paths with a plurality of separate heat pipes.

18. The method of claim 17, further comprising:
positioning each heat pipe of the plurality of heat pipes to extend a distance away from the heat sink.

19. The method of claim 18, further comprising:
housing all of the transmitter coil, the heat sink, and the plurality of heat pipes within a housing;
wherein the housing includes a subject side and an environment side;
wherein the plurality of heat pipes extend to the environment side away from the heat sink.

20. The method of claim 19, further comprising:
operating the wireless recharger to energize the transmitter coil to generate the power transfer signal and thereby, generate thermal energy;
wherein a temperature differential between a position near the transmitter coil and a position away from the transmitter coil causes a transfer of thermal energy via the heat pipes away from the heat sink.

* * * * *